United States Patent
Hendrix, III et al.

(10) Patent No.: US 9,474,274 B2
(45) Date of Patent: Oct. 25, 2016

(54) CANOLA SEED TREATMENT COMPOSITION AND METHOD

(71) Applicant: Dow AgroSciences LLC, Indianapolis, IN (US)

(72) Inventors: William H. Hendrix, III, Indianapolis, IN (US); Gary C. Turnbull, Winnipeg (CA)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 14/206,306

(22) Filed: Mar. 12, 2014

(65) Prior Publication Data

US 2014/0274686 A1    Sep. 18, 2014

Related U.S. Application Data

(60) Provisional application No. 61/781,061, filed on Mar. 14, 2013.

(51) Int. Cl.
| | |
|---|---|
| *A01N 43/22* | (2006.01) |
| *A01N 25/00* | (2006.01) |
| *A01N 43/36* | (2006.01) |
| *A01N 43/653* | (2006.01) |
| *A01N 51/00* | (2006.01) |

(52) U.S. Cl.
CPC ............... *A01N 43/22* (2013.01); *A01N 25/00* (2013.01); *A01N 43/36* (2013.01); *A01N 43/653* (2013.01); *A01N 51/00* (2013.01)

(58) Field of Classification Search
None
See application file for complete search history.

(56) References Cited

U.S. PATENT DOCUMENTS

| | | |
|---|---|---|
| 8,293,680 B2 | 10/2012 | Lindholm et al. |
| 2011/0160054 A1* | 6/2011 | Breuningger et al. ........ 504/100 |
| 2011/0269804 A1 | 11/2011 | Cassayre et al. |
| 2011/0275518 A1 | 11/2011 | Marques et al. |

FOREIGN PATENT DOCUMENTS

| | | |
|---|---|---|
| WO | WO 2011014720 A1 * | 2/2011 |
| WO | 2012080415 A1 | 6/2012 |
| WO | 2013015993 A1 | 1/2013 |

OTHER PUBLICATIONS

International Search Report and Written Opinion, Jul. 7, 2014, pp. 1-7, International Searching Authority, Alexandria, Virginia.

* cited by examiner

*Primary Examiner* — Abigail Fisher
*Assistant Examiner* — Daniel Branson
(74) *Attorney, Agent, or Firm* — Yung H. Lee; Taft Stettinius & Hollister

(57) ABSTRACT

Canola seed treated with spinetoram controls flea beetle.

6 Claims, No Drawings

CANOLA SEED TREATMENT COMPOSITION AND METHOD

CROSS REFERENCE TO RELATED APPLICATIONS

This application claims the benefit of U.S. Provisional Patent Application Ser. No. 61/781,061 filed Mar. 14, 2013, the entire disclosure of which is hereby expressly incorporated by reference.

FIELD OF THE INVENTION

The present invention relates to a seed treatment method for canola seeds.

BACKGROUND

The importance of using an insecticide seed treatment for protection against flea beetles in canola production is well known. (see, e.g., Knodel et al. 2006 Insecticide Efficacy against Flea Beetles on Canola Trial A., www.ag.ndsu.edu/archive/langdon/06data/fbsyngenta06.pdf). HELIX® (thiamethoxam), GAUCHO®600 (600 g/L imidacloprid), and PONCHO® 600 (600 g/L clothianidin) insecticide seed treatments are registered for use on canola.

US 2011/0263429 discloses pesticidal combinations comprising spinetoram for seed treatment.

There remains a need for insecticide seed treatments for canola seed that provide improved performance.

SUMMARY OF THE INVENTION

In some embodiments, the invention provides a method of protecting canola from flea beetles by treating canola seeds with spinetoram.

In some embodiments the invention provides a method of protecting canola from flea beetles which comprises treating canola seeds with a combination of spinetoram and one or more additional systemic insecticides.

In some embodiments, the invention provides a method of protecting canola from flea beetles which comprises treating canola seeds with a combination comprising spinetoram and one or more fungicides.

In some embodiments, the invention provides canola seed that has been treated with spinetoram.

In some embodiments, the invention provides canola seed that has been treated with a combination of spinetoram and one or more additional systemic insecticides.

DETAILED DESCRIPTION OF THE INVENTION

Definitions

As used herein, the following terms have the indicated meanings:

The term "spinetoram" refers to a semi-synthetic derivative of spinosyn fermentation products comprising a mixture of compounds that includes 50-95% of a first compound referred to as the "major component" and 50-5% of a second compound referred to as the "minor component". Spinetoram's activity and applications are summarized in Tomlin, C., ed. A World Compendium The Pesticide Manual. 15$^{th}$ ed. Alton: BCPC Publications, 2009 (hereafter "*The Pesticide Manual*"). Additional information regarding spinetoram is found in "Compendium of Pesticide Common Names" located at http://www.alanwood.net/pesticides/index.html as of the filing date of this document.

The term "clothianidin" refers to [C(E)]-N-[(2-chloro-5-thiazolyl)methyl]-N'-methyl-N"-nitroguanidine, an insecticide. Its structure, activity and applications are summarized in *The Pesticide Manual*.

The term "difenoconazole" refers to 1-[2-[2-chloro-4-(4-chlorophenoxy)phenyl]-4-methyl-1,3-dioxolan-2-ylmethyl]-1H-1,2,4-triazole, a fungicide. Its structure, activity and applications are summarized in *The Pesticide Manual*.

The term "fludioxonil" refers to 4-(2,2-difluoro-1,3-benzodioxol-4-yl)-1H-pyrrole-3-carbonitrile, a fungicide. Its structure, activity and applications are summarized in *The Pesticide Manual*.

The term "metalaxyl-M" refers to methyl N-(2,6-dimethylphenyl)-N-(methoxyacetyl)-D-alaninate, a fungicide. Its activity and applications are summarized in *The Pesticide Manual*.

The term "thiamethoxam" refers to 3-[(2-chloro-5-thiazolyl)methyl]tetrahydro-5-methyl-N-nitro-4H-1,3,5-oxadiazin-4-imine, an insecticide. Its structure, activity and applications are summarized in *The Pesticide Manual*.

The term "HELIX® XTra Seed Treatment" refers to a seed treatment product of Syngenta Crop Protection that contains, as active ingredients: thiamethoxam 20.70%, difenoconazole 1.25%, metalaxyl-M and S-isomer 0.39%, and fludioxonil, 0.13%.

The term "Tribune™ Seed Treatment" refers to a seed treatment product of Syngenta Crop Protection that contained difenoconazole 1.61%, metalaxyl-M 0.51%, and fludioxonil, 0.17%.

The term "imidacloprid" refers to (2E)-1-[(6-chloro-3-pyridinyl)methyl]-N-nitro-2-imidazolidinimine, a systemic insecticide. Its structure, activity and applications are summarized in *The Pesticide Manual*.

Methods for Treating Canola Seeds

In some embodiments of the invention, canola seed is treated with from about 0.1 to about 1 mg/seed of spinetoram. In some embodiments, canola seed is treated with from about 0.2 to about 0.6 mg/seed of spinetoram. In some embodiments canola seed is treated with spinetoram at a rate of about 4 g/kg of seed.

In some embodiments of the invention, canola seed is treated with spinetoram and at least one other systemic insecticide. The other insecticide can be any systemic insecticide approved for treatment of canola seed. Examples include thiamethoxam, imidacloprid, and clothianidin. In a certain embodiment of the invention canola seed is treated with a combination of spinetoram, and thiamethoxam.

In some embodiments of the invention, canola seed is treated with a combination of spinetoram and at least one fungicide. The fungicide can be any fungicide approved for treatment of canola seed. Examples include difenoconazole, metalaxyl-M isomer and fludioxonil. In a certain embodiment of the invention, canola seed is treated with a combination of spinetoram, difenoconazole, metalaxyl-M isomer and fludioxonil.

In some embodiment of the invention, canola seed is treated with a combination of spinetoram, at least one additional systemic insecticide, and at least one fungicide. In a certain embodiment, canola seed is treated with spinosad, thiamethoxam, difenoconazole, metalaxyl-M isomer and fludioxonil.

Equipment and protocols for treating seed are well known in the art, and are described, e.g., in US 2011/0263429, which is incorporated herein by reference.

EXAMPLES

Example 1

Field Efficacy Trial for Canola Seed Treatment

Four samples of canola seed were treated, each sample with a different one of the four seed treatment compositions listed below:
1) standard HELIX® XTra Seed Treatment,
2) standard HELIX® XTra Seed Treatment plus 4 g ai/kg of spinetoram;
3) standard Tribune™ Seed Treatment,
4) standard Tribune™ Seed Treatment plus 4 g ai/kg of spinetoram.

The treated seed was evaluated in small plot trials to evaluate efficacy of the treatments to control flea beetle damage.

Small plot trials were carried out at multiple locations in Canada. Canola plant stand, plant cover, canola defoliation, and feeding damage were evaluated at intervals, with the following results:

A 2 to 5% increase in visual canola plant stand was observed 1-4 weeks after emergence when spinetoram was added to HELIX® XTra Seed Treatment. There was a 15 to 20% increase in visual canola plant stand 1-4 weeks after emergence when spinetoram was added to Tribune™ Seed Treatment. At two locations a visual assessment of canola plant stand 2-3 weeks after emergence showed a 30-35% increase when spinetoram was added to Helix Extra Seed Treatment and a 10-20% increase when spinetoram was added to Tribune™ Seed Treatment.

Across three locations 2-4 weeks after emergence there was 40% defoliation of canola treated with Tribune™ Seed Treatment alone versus 18-20% for canola treated with the combination of Tribune™ Seed Treatment and spinetoram, and there was 16% defoliation of canola treated with HELIX® XTra Seed Treatment alone versus 12% defoliation of canola treated with the combination of HELIX® XTra Seed Treatment and spinetoram.

Across four locations when flea beetle feeding damage 2-4 weeks after emergence is expressed as a percentage of damage observed with Tribune™ Seed Treatment alone, there was a 40% reduction with the combination of Tribune™ Seed Treatment plus spinetoram, a 55% reduction with HELIX® XTra Seed Treatment alone and a 65% reduction with the combination of HELIX® XTra Seed Treatment plus spinetoram.

What we claim is:

1. A method of treating canola seed to protect canola from flea beetle damage which comprises applying to the canola seed a combination of spinetoram and a seed treatment composition comprising thiamethoxam, difenoconazole, metalaxyl-M isomer and fludioxonil, wherein the spinetoram is applied to the canola seed at a rate of about 4 g/kg.

2. The method according to claim 1 wherein the seed treatment composition comprises 20.70% thiamethoxam, 1.25% difenoconazole, 0.39% metalaxyl-M isomer and 0.13% fludioxonil.

3. A treated canola seed comprising difenoconazole, metalaxyl-M isomer, fludioxonil and about 4/kg of spinetoram.

4. The treated canola seed according to claim 3, further comprising thiamethoxam.

5. A method of treating canola seed to protect canola from flea beetle damage which comprises applying to the canola seed a combination of spinetoram and a seed treatment composition comprising difenoconazole, metalaxyl-M and fludioxonil, wherein the spinetoram is applied to the canola seed at a rate of about 4 g/kg.

6. The method according to claim 5 wherein the seed treatment composition comprises 1.61% difenoconazole, 0.51% metalaxyl-M and 0.17% fludioxonil.

* * * * *